(12) United States Patent
Pohjonen et al.

(10) Patent No.: US 7,135,025 B2
(45) Date of Patent: Nov. 14, 2006

(54) SURGICAL IMPLANT

(75) Inventors: Timo Pohjonen, Tampere (FI); Timo Reunämaki, Tampere (FI); Auvo Kaikkonen, Tampere (FI); Jan Nieuwenhuis, Gorinchem (NL); Pia Ahvenjärvi, Tampere (FI)

(73) Assignee: Inion Ltd., Tampere (FI)

( * ) Notice: Subject to any disclaimer, the term of this patent is extended or adjusted under 35 U.S.C. 154(b) by 0 days.

(21) Appl. No.: 10/200,561

(22) Filed: Jul. 22, 2002

(65) Prior Publication Data

US 2003/0199878 A1 Oct. 23, 2003

(30) Foreign Application Priority Data

Apr. 22, 2002 (FI) .................... 20020772

(51) Int. Cl.
*A61B 17/58* (2006.01)
*A61F 2/08* (2006.01)

(52) U.S. Cl. .................... 606/73; 606/77; 623/13.14

(58) Field of Classification Search .................... 606/73, 606/77, 70, 71, 72, 75, 76, 151, 154; 623/13.11, 623/13.14, 11.11, 23.75; 528/354, 355; 525/413, 415, 419, 420; 523/115, 105, 113, 523/114; 424/486, 426
See application file for complete search history.

(56) References Cited

U.S. PATENT DOCUMENTS

| | | | | |
|---|---|---|---|---|
| 4,008,303 A * | 2/1977 | Glick et al. | .................... | 264/78 |
| 4,142,293 A | 3/1979 | Tieche | .................... | 32/15 |
| 4,435,590 A | 3/1984 | Shalaby et al. | .................... | 560/61 |
| 4,605,730 A * | 8/1986 | Shalaby et al. | .................... | 528/357 |
| 4,689,424 A * | 8/1987 | Shalaby et al. | .................... | 560/61 |
| 4,776,329 A | 10/1988 | Treharne | .................... | 128/92 YR |
| 4,905,679 A | 3/1990 | Morgan | .................... | 606/70 |
| 4,973,333 A | 11/1990 | Treharne | .................... | 606/77 |
| 5,108,399 A | 4/1992 | Eitenmuller et al. | .................... | 606/77 |
| 5,275,601 A | 1/1994 | Gogolewski et al. | .................... | 606/72 |
| 5,522,897 A * | 6/1996 | King et al. | .................... | 606/102 |
| 5,569,250 A | 10/1996 | Sarver et al. | .................... | 606/69 |
| 5,601,429 A | 2/1997 | Blacklock | .................... | 433/174 |
| 5,601,553 A | 2/1997 | Trebing et al. | .................... | 606/61 |
| 5,681,873 A * | 10/1997 | Norton et al. | .................... | 523/115 |
| 5,800,542 A | 9/1998 | Li | .................... | 623/11 |
| 5,868,749 A | 2/1999 | Reed | .................... | 606/76 |
| 6,030,554 A * | 2/2000 | Ichihara | .................... | 252/583 |
| 6,060,007 A * | 5/2000 | Hutton et al. | .................... | 264/78 |
| 6,235,869 B1 * | 5/2001 | Roby et al. | .................... | 528/354 |
| 6,269,716 B1 | 8/2001 | Amis | .................... | 81/121.1 |
| 6,343,531 B1 | 2/2002 | Amis | .................... | 81/121.1 |

(Continued)

FOREIGN PATENT DOCUMENTS

EP       0 714 633       6/1996

(Continued)

OTHER PUBLICATIONS

Athanasiou et al., "Sterilization, toxicity, biocompatibility and clinical applications of polyactic acid/polyglycolic acid copolymers", *Biomaterials*, 17(2):93-102, 1996.

(Continued)

*Primary Examiner*—Pedro Philogene
(74) *Attorney, Agent, or Firm*—Banner & Witcoff, Ltd.

(57) ABSTRACT

A surgical implant made of a polymer, copolymer, polymer mixture or polymer composite that dissolves in the organ system. The manufacturing material is dyed with the coloring agent D&C Violet No. 2 or D&C Green No. 6. Preferably, the amount of the coloring agent is at most approximately 0.03 percent by weight and the implant is sterilized by radiation.

12 Claims, 1 Drawing Sheet

U.S. PATENT DOCUMENTS

| | | | |
|---|---|---|---|
| 6,352,667 B1 | 3/2002 | English | 264/328.17 |
| 6,477,923 B1 | 11/2002 | Amis | 81/121.1 |

FOREIGN PATENT DOCUMENTS

| | | |
|---|---|---|
| EP | 1 093 824 | 4/2001 |
| WO | WO 99/07418 | 2/1999 |
| WO | WO 00/01307 | 1/2000 |

OTHER PUBLICATIONS

Brinston, "Gaining the Competitive Edge with Gamma Sterilization", *Medical Device Technology*, pp. 29-33, 1991.

*Wound Closure Biomaterials and Devices*, Eds. Chu, von Fraunhofer, and Greisler, CRC Press, Inc., pp. 183-184, 1997.

Kivijärvi, "Ja siihen liityviä materiaalinvalinta- ja pakkausnäkökohtia", *Pakkaus*, 5:32-35, 1983.

Kivijärvi, Gammasäteilyn Käyttömahdollisuuksista Lääketeollisuudessa, *Acta Pharma. Fenn.*, 92:9-17, 1983.

König et al., "Autosterilization of Biodegradable Implants by Injection Molding Process", *J. Biomed. Mater. Res.*, 38:115-119, 1997.

Pelto-Vasenius et al., "Redisplacement after ankle osteosynthesis with absorbable implants", *Arch. Orthop. Trauma Surg.*, 117:159-162, 1998.

English abstract of EP 1 093 824.

R. Suuronen, P. Lane, E. Sarkiala, T. Pohjonen, and C. Lindqvist: *Sagittal split osteotomey fixed with bidegradable, self-reinforced poly-L-lactide screws. A pilot study in sheep.*. Int. J. Oral Maxillofac. Surg. 1992:21:303-308.

International Standard, ISO 5835 First Edition Jan. 15, 1991 *Implants for surgery-Metal bone screws with hexagonal drive connection, spherical under-surface of head, asymmetrical thread-Dimensions*.

H. Peltoniemi, R. Tulamo, H. Pihlajamaki, M. Kallioinen, T. Pohjonen, P. Tormala, P. Rokkanen, and T. Waris: *The Healing of Cranial Osteomy Lines Fixed with SR-PLLA Plates and Titanium Screws: an Experimental Study in Growing Sheep*. Transactions of the 11$^{th}$ Congress of the International Confederation of Plastic, Reconstructive and Aesthetic Surgery, p. 630, Yokohama, Japan, Apr. 16-21, 1995.

B. Eppley and A.M. Sadove: *A Comparison of Resorbable and Metallic Fixation in Healing of Calvarial Bone Grafts*. Plastic and Reconstructive Surgery, vol. 96, No. 2 Aug. 1995.

\* cited by examiner

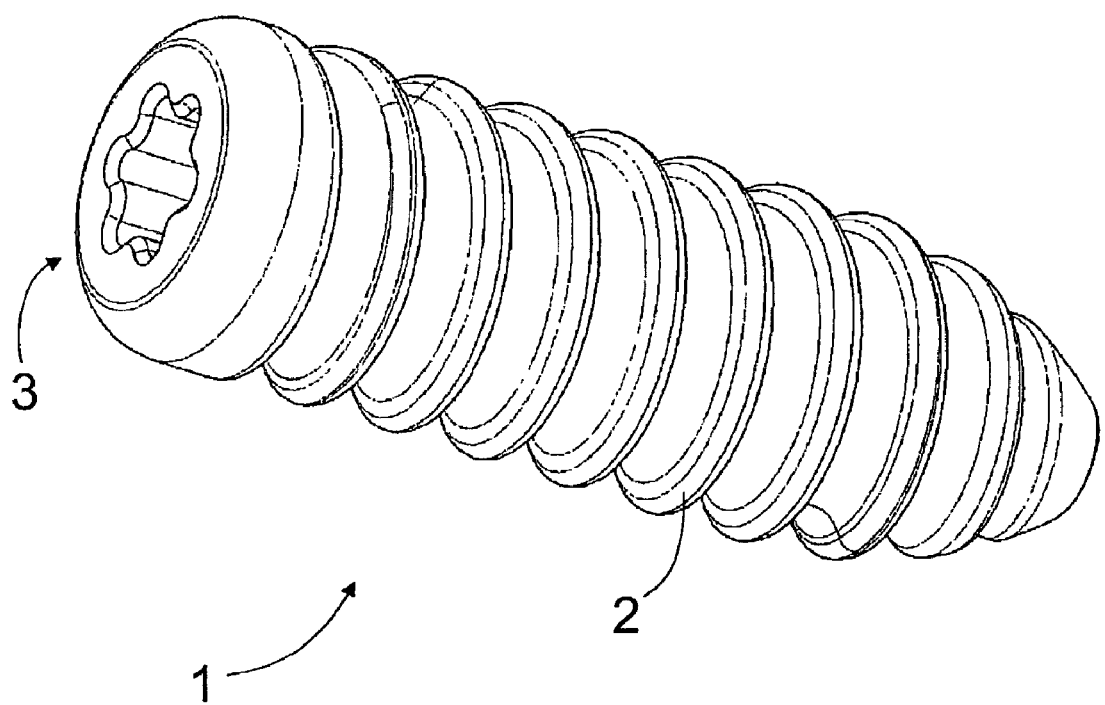
Fig.

US 7,135,025 B2

SURGICAL IMPLANT

FIELD OF THE INVENTION

This application claims priority from Finnish patent application number FI 20020772, filed 22 Apr. 2002.

The invention relates to a surgical implant made of a polymer, copolymer, polymer mixture or polymer composite that dissolves in the organ system.

BACKGROUND OF THE INVENTION

Surgical implants made of materials absorbing into the organ system, i.e. biodegradable materials, are known. Their use in surgery is continuously increasing, because they offer a significant advantage over conventional implants made of metal: they need not be removed from the system after the operated tissue has healed. This way, it is possible to avoid surgery to remove the implant, which is naturally advantageous with respect to patient satisfaction, resource load and costs.

However, metal provides the advantage over biodegradable materials that an implant made of metal is quite well distinguishable from the tissue of the organ system. Good visual distinguishability facilitates considerably the work of the surgeon in implanting the implant in the correct position and in the correct manner into the organ system. Biodegradable materials are typically translucent and light-colored and consequently, an implant made of them is poorly distinguishable from tissue. For instance, in anterior cruciate ligament ACL or posterior cruciate ligament PCL reconstruction, either a soft tissue graft, which can typically be a hamstring graft, for instance, or a bone-tendon-bone graft is fastened to holes made at the ends of the femur or tibia. The operation is usually performed as an endoscopic operation. It is of primary importance that the surgeon easily and reliably sees the position and location of the used fixation means, such as interference screws, pins or wedges, in the object being operated. This is not always the case when using biodegradable fixation means.

Coloring agents have been routinely used in dyeing biodegradable sutures since the beginning of their use, i.e. for over 20 years. One problem with dyed biodegradable sutures is that they cannot be radiation sterilized using the conventional $^{60}$Co gamma radiation process, because the polymers used in their preparation split too much under radiation and the suture does not keep its strength long enough for the tissue to heal properly (*Wound Closure Biomaterials*, Ed. C. C. Chu et al. CRC Press 1997, Boca Raton, Fla., U.S.A, page 183). Thus, they need to be sterilized by methods that do not split the suture material.

Implants made of biodegradable materials are known that are dyed with a coloring agent to improve their visibility. Due to the above-mentioned problems with dyed sutures, the dyed implants are not sterilized by radiation but with ethylene oxide (EO), for instance, (Athanasiou, K. A. et al., *Biomaterials* 17 (1996) 93 to 102). An advantage of EO sterilization is that it does not affect the implant material or its additives, such as the color pigment. A problem with EO sterilization is a possible toxic EO residue that remains in the polymer. The EO sterilization process is, therefore, time consuming, complex and expensive. The EO residue needs to be removed from the material with an aeration period that is performed in a sterilization chamber and takes several days. In addition, the packing process of the product has two phases and is, therefore, difficult. The surgical implant must first be packed in material that allows EO gas to penetrate, for instance in a Tyvec© bag. On top of this, a packing material is required to protect the product from moisture, such as an aluminized plastic bag. Because aluminized plastic does not allow EO gas to penetrate, it can be seamed tight only after the first sterilization/aeration period. The use of an aluminum bag in an operating theater also requires that the aluminum bag be sterilized on the outside. This is why after seaming the aluminum bag, a third layer of an EO gas permeable Tyvec© bag is put on the aluminum bag, and the outside of the aluminum bag is sterilized in a second sterilization phase. All in all, EO sterilization is a complex and quite expensive sterilization method.

Even though coloring agents have long been used in suture materials, their use in implants is still rare and limited to small-sized implants sterilized with EO gas. An example of such a product is a Meniscal BioStinger® arrow dyed with Violet D&C No. 2 pigment and used in treating meniscus ruptures, which is marketed by Linvatec Corporation, Largo, Fla., U.S.A., and another example, in which D&C Violet No. 2 pigment is used, is a S-D-sorb™ E-Z Tac anchor used in treating joint capsules of the humerus, which is marketed by Surgical Dynamics Inc., Norwalk, Conn., U.S.A. The chemical name of D&C Violet No. 2 pigment is 1,4-hydroxy[(4-methylphenyl)amino]-9,10-anthracenedion (CAS No. 81-48-1). The amount of color pigment used in biodegradable sutures and small-sized implants usually varies between 0.1 and 0.3 percent by weight as calculated from the weight of the implant. As high an amount of color pigment as this, which is acceptable in small-sized implants, increases the number of tissue reactions when the operation requires one or more large implants (Pelto-Vasenius K., et al. *Arch. Orthop. Trauma Surg.* (1998)117: 159 to 162).

BRIEF DESCRIPTION OF THE INVENTION

The purpose of this invention is to provide a novel and improved surgical implant.

The surgical implant of the invention is characterized in that the manufacturing material is dyed with the coloring agent D&C Green No. 6 or D&C Violet No. 2.

One preferred embodiment of the surgical implant of the invention is characterized in that the amount of the coloring agent is at most approximately 0.03 percent by weight.

A second preferred embodiment of the surgical implant of the invention is characterized in that the implant is sterilized by radiation.

The invention provides the advantage that the color of the implant is easily distinguished from tissue, whereby it is easy for the surgeon to note the position and location of the implant in the object being operated. This speeds up the operation and improves its quality. In addition, the implant is sterilized by radiation, for instance D&C Green No. 6 by gamma radiation or electron radiation, or D&C Violet No. 2 by electron radiation that are fast and inexpensive sterilization methods.

BRIEF DESCRIPTION OF THE FIGURES

The invention is described in greater detail in the attached drawing which is a simplified schematic perspective view of an implant of the invention.

DETAILED DESCRIPTION OF THE INVENTION

FIG. 1 is a schematic perspective view of an implant of the invention. The implant is an interference screw 1 used in ACL/PCL reconstruction. Depending on the applied operating principle, a soft tissue graft or a bone-tendon-bone graft is fastened with the interference screw 1 to holes made at the ends of the femur or tibia. The ACL/PCL reconstruction operation is known per se to a person skilled in the art and is thus not described in more detail herein.

The interference screw 1 has a thread 2, with which the screw fastens to the bone hole. The interference screw 1 also has a driving socket 3 for screwing the screw 1 into the bone hole by means of an instrument.

The interference screw 1 is made of a polymer, copolymer, polymer mixture or polymer composite that dissolves in the organ system. The manufacturing material is a cyclic ester polymer, copolymer, polymer mixture or polymer composite that can be copolymerized for instance with lactic acid, L-lactide, D-lactide, D,L-lactide, mesolactide, glycolic acid, glycolide or the like and optionally also with some other lactide. The manufacturing material can also comprise other comonomers providing desired properties to the material, such as $\alpha$-, $\beta$- and $\gamma$-hydroxy butyric acid, $\alpha$-, $\beta$- and $\gamma$-hydroxy valerianic acid and other hydroxy fatty acids ($C_{11}$ to $C_{25}$), such as stearic acid, palmitinic acid, oleic acid, lauric acid and the like. The manufacturing material can thus be polylactide, polyglycolide, poly(L-lactide), poly(D-lactide), poly(L-lactide-co-D,L-lactide), poly(L-lactide-co-mesolactide), poly(L-lactide-co-glycolide), poly(L-lactide-co-$\epsilon$-caprolactone), poly(D, L-lactide-co-mesolactide), poly(D, L-lactide-co-glycolide), poly(D,L-lactide-co-$\epsilon$-caprolactone), poly(mesolactide-co-glycolide), poly(mesolactide-co-$\epsilon$-caprolactone) or the like. The monomer units of the copolymer basic material can be present in ratios from 50:50 to 85:15 or some other ratio within this range. Suitable copolymeric manufacturing materials include poly(L-lactide-co-D,L-lactide) 70:30, poly(L-lactide-co-D,L-lactide) 80:20, poly(L-lactide-co-glycolide) 85:15 and poly(L-lactide-co-glycolide) 80:20.

The manufacturing material can also contain trimethylene carbonate or dioxanone. Such manufacturing materials include poly(L-lactide-co-trimethylenecarbonate), poly(D, L-lactide-co-trimethyleneca rbonate), poly(mesolactide-co-trimethylenecarbonate), poly(glycol-co-trimethylenecarbonate), poly(L-lactide-co-dioxanone), poly(D,L-lactide-co-dioxanone), poly(mesolactide-co-dioxanone), poly(glycol-co-dioxanone) and the like.

Poly(L-lactide), poly(L-lactide-co-D,L-lactide), poly(L-lactide-co-trimethylenecarbonate) and their mixtures are especially preferable manufacturing materials.

It should be noted that the polymers and copolymers suitable as the manufacturing material are known per se and they can easily be prepared by preparation methods known per se to a person skilled in the art.

D&C Green No. 6, chemical name 1,4-bis[(4-methylphenyl)amino]-9,10-anthracenedion (CAS No. 128-80-3) or D&C Violet No. 2, chemical name 1,4-hydroxy[(4-methylphenyl)amino]-9,10-anthracenedion (CAS No. 81-48-1), both coloring agents accepted and named by FDA (Food and Drug Administration), is mixed with the manufacturing material. D&C Green No. 6 has obtained FDA approval (21CFR74.3206) for use in dyeing biodegradable sutures used in general surgery or ophthalmic surgery. D&C Violet No. 2 is approved (21CFR74.3602) for use in various sutures and biodegradable meniscus clamps made of a poly(L-lactic acid) material.

The coloring agent can be mixed in a suitable amount as such with the manufacturing material of the implant. The mixing can be done by dry mixing a suitable amount of the coloring agent in powder form with the polymer in granulate, crush or powder form and by thereafter melting the mixture in the manner of a conventional undyed material in the cylinder of a melt machine tool, such as an injection-molding machine or extruder. The mixing can also be done by dissolving the coloring agent in a suitable solvent, such as ethanol, and by mixing the granulated, crushed or powdered polymer that does not dissolve in the used solvent with the solvent dyed with the coloring agent. After the solvent dissolves, the coloring agent is evenly distributed on the surface and pores of the polymer and it can be processed as described above. Further, it is possible to use a solvent into which both the polymer and the coloring agent dissolve, and to proceed after the dissolving and the re-crushing of the dyed polymer as described above. D&C Green No. 6 or D&C Violet No. 2—later coloring agent—can also be mixed with the manufacturing material in such a manner that an amount of the coloring agent that is bigger than the intended coloring agent concentration of the implant is first mixed with a part of the manufacturing material. In other words, a master batch is prepared of the coloring agent and the manufacturing material. The master batch can for instance be a mixture with 1 to 10 percent by weight of the coloring agent. It should be noted in this context that all percentages given in this application are percentages by weight, calculated from the total mass of the manufacturing material and coloring agent. Such an amount of the master batch is mixed with the manufacturing material that the desired coloring agent content is achieved in the manufacturing material.

The amount of the coloring agent in the finished implant is at most approximately 0.03%. Only this amount of the coloring agent is required, because an implant dyed in this manner is sufficiently visible, even better visible than a corresponding metal implant. In addition, with the increase in the amount of the coloring agent, the risk of tissue reactions, such as swelling and pain, caused by the coloring agent increases (Pelto-Vasenius K., et al. *Arch. Orthop. Trauma Surg.* (1998) 117: 159 to 162).

In large implants in particular, such as interference screws and other fixation means used in ACL/PCL operations, the absolute amount of the coloring agent may rise quite high. Therefore, it is advantageous to keep the coloring agent content as low as possible in the implant. The coloring agent content is preferably 0.002 to 0.02%. The implant is then sufficiently distinguishable from tissue, but the amount of the coloring agent is so small that tissue reactions are highly improbable even though the implant was a large one.

The implant of the invention can be made using manufacturing methods known per se, such as extrusion, casting, injection molding, compression, thermoforming or the like.

The implant is sterilized by gamma radiation or electron radiation. The dose absorbed in radiation is preferably over 10 kGy so as to ensure a sterility assurance level (SAL) of $10^{-6}$.

The advantages of radiation sterilization are described in greater detail in a number of publications. A generally approved radiation dose providing the sterility assurance level (SAL) of $10^{-6}$ in implants is 25 kGy. Unfortunately, this high a dose of high-energy radiation reduces the molecular weight of polymer by approximately 40% (König C., et al. *J. Biomed. Mater. Res.* 38 (1997), pages 115 to 119). High-energy radiation can also cause alterations in the chemical structure of color pigments. The insides of implants made by injection molding at a high temperature are sterile after the process (König C., et al. *J. Biomed. Mater. Res.* 38 (1997), pages 115 to 119). In practice, the products must be processed to some extent after injection molding, after which at least the surface of the product requires sterilization. However, this requires a lower radiation dose. Injection-molded implants made at least partly in a clean room of at least classification 10,000 can obtain the sterility assurance level (SAL) of $10^{-6}$ already at a radiation dose of 10 kGy. The same assurance level can also be obtained with said radiation dose for implants made using other melt machining techniques, such as extrusion, and manufactured at least partly in a clean room of at least classification 10,000.

EXAMPLE 1

The coloring agent D&C Green No. 6 was dissolved in a first batch of ethanol and D&C Violet No. 2 in a second batch of ethanol. Both coloring agent solutions were gamma-radiated such that the absorbed dose was over 25 kGy.

It was noted that the color of the first D&C Violet No. 2-dyed solution disappeared completely during radiation. However, there was a barely noticeable color alteration in the second D&C Green No. 6-dyed solution. The slight color alteration of the second solution was probably due to the fact that the coloring agent D&C Green No. 6 was prepared using as starting material the coloring agent D&C Violet No. 2, from which a 1.2-percent by weight residue remained in the coloring agent D&C Green No. 6. The disappearance of said residue caused the slight color alteration in the second solution from bluish green to bright green.

EXAMPLE 2

A master batch No. 1 was prepared from the coloring agent D&C Green No. 6 (Neelikon Food Dyes & Chemicals Ltd, India) and poly(L-lactide-co-D,L-lactide) 80:20 polymer crush (Purasorb PLD, Purac biochem b.v., the Netherlands) by dry mixing 0.3 grams of the coloring agent and 100 grams of the polymer in a Turbula T2F mixer during 30 minutes.

At the next stage, a polymer raw material mix No. 1 was dry mixed in a Turbula T2F mixer during 30 minutes, the materials in the mix being: A) poly(L-lactide-co-D,L-lactide) 80:20 polymer crush (Purasorb PLD, Purac biochem b.v., the Netherlands), B) poly(L-lactide-co-trimethylenecarbonate) 70:30 polymer crush (Resomer LT706, Boehringer Ingelheim Pharma KG, Germany), and C) the above-mentioned master batch No.1 at A:B:C=83.7:15:1.3. The color content of the thus prepared raw material mix No. 1 was calculated to be 0.0039%.

500 pieces of dyed biodegradable Ø 7×20 mm ACL screws were made of the raw material mix No. 1 by using a Fanuc Roboshot Alpha i50A injection-molding machine. The temperature of the cylinder of the injection-molding machine was 210° C. and the injection pressure was 2000 bar. A part of the screws were re-crushed into granulate and the crush was used to make Ø 40×2 mm sheets with a Collin P300 charge compressor for a spectrophotometric color analysis.

In addition, a master batch No. 2 was prepared from the coloring agent D&C Violet No. 2 (Neelikon Food Dyes & Chemicals Ltd, India) and poly(L-lactide-co-D,L-lactide) 80:20 polymer crush (Purasorb PLD, Purac biochem b.v., the Netherlands) by dry mixing 0.3 grams of the coloring agent and 100 grams of the polymer in a Turbula T2F mixer during 30 minutes.

As above, at the next stage, a polymer raw material mix No. 2 was dry mixed in a Turbula T2F mixer during 30 minutes, the materials in the mix being: A) poly(L-lactide-co-D,L-lactide) 80:20 polymer crush (Purasorb PLD, Purac biochem b.v., the Netherlands), B) poly(L-lactide-co-trimethylenecarbonate) 70:30 polymer crush (Resomer LT706, Boehringer Ingelheim Pharma KG, Germany), and C) the above master batch No. 2 at A:B:C=83.7:15:1.3.

The color content of the raw material mix No. 2 was also calculated to be 0.0039%. 500 pieces of dyed biodegradable Ø 7×20 mm ACL screws were made of the raw material mix No. 2 by using a Fanuc Roboshot Alpha i50A injection-molding machine. As above, the temperature of the cylinder of the injection-molding machine was 210° C. and the injection pressure was 2000 bar. A part of the screws were re-crushed into granulate and the crush was used to make Ø 40×2 mm sheets with a Collin P300 charge compressor for a spectrophotometric color analysis.

Implants made of both raw material mixes 1 and 2 and sheets made for the color analysis were gamma and electron (E beam) radiated so that the absorbed doses in both radiation methods were 15 and 25 kGy. The color of the sheet samples was analyzed before and after sterilization in a HunterLab Utrascan XE spectrophotometer. The results of the color analysis L* (luminosity), a* (value on the red-green scale) and b* (value on the yellow-blue scale) are shown in Table 1.

Visually, it was noted that the color of the implants dyed with the coloring agent D&C Violet No. 2 turned a great deal lighter due to the 25-kGy gamma radiation and the resulting color was not acceptable for the use of the implant. In the color analysis, the difference in comparison with a non-sterilized sample showed in that especially the blue color weakened. In Table 1, the difference is shown as a strong positive trend of the b* value. The red tone also weakened clearly, in other words, the a* value changed towards negative. Visually, the difference showed in that the original bright violet changed into a dull grayish color. With the 15-kGy gamma radiation dose, the violet tone also weakened clearly. The 25-kGy electron radiation changed the violet tone clearly less than an equal gamma radiation dose and the 15-kGy electron radiation dose produced a fully acceptable color for the use of the implant.

Correspondingly, the color of the implants dyed with the coloring agent D&C Green No. 6 did not show an as significant change visually after radiation. At a 25-kGy gamma dose, the bright blue-green tone of the color changed into a slightly duller green, but was still acceptable for the use of the implant. At a 15-kGy gamma dose and 25-kGy electron radiation dose, the difference in comparison with a non-sterilized sample was difficult to detect visually and at a 15-kGy electron radiation dose, no difference could be detected.

TABLE 1

The results of the spectrophotometric analysis

| Sample | Method | Dose (kGy) | L* | a* | b* |
| --- | --- | --- | --- | --- | --- |
| Viol 0 | Non-sterilized | 0 | 69.2 | 9.0 | −23.8 |
| Viol 15 | Gamma radiation | 15 | 72.4 | 5.6 | −12.9 |
| Viol 25 | Gamma radiation | 25 | 74.1 | 4.2 | −8.5 |
| Viol E15 | Electron radiation | 15 | 70.5 | 7.3 | −16.5 |
| Viol E25 | Electron radiation | 25 | 73.3 | 5.0 | −12.7 |
| Green 0 | Non-sterilized | 0 | 71.3 | −24.2 | 11.1 |
| Green 15 | Gamma radiation | 15 | 72.8 | −18.7 | −5.6 |
| Green 25 | Gamma radiation | 25 | 73.1 | −17.3 | −2.7 |
| Green E15 | Electron radiation | 15 | 72.5 | −22.3 | −9.5 |
| Green E25 | Electron radiation | 25 | 72.4 | −20.1 | 7.1 |

When the visibility of the coloring agents in endoscopic surgery of the knee area were compared in cadaver tests, it was unexpectedly detected that a screw dyed with the coloring agent D&C Green No. 6 was clearly distinguishable from tissue on the screen of the display, whereas even the best screw dyed with D&C Violet No. 2 was clearly less distinguishable.

Radiation sterilization can be done not only with gamma and electron radiation, but also with other short-wave high-energy radiation, such as x-radiation, ultraviolet radiation and microwave radiation.

The drawings and the related description are only intended to illustrate the idea of the invention. The invention may vary in detail within the scope of the claims. Thus, in addition to an ACL/PCL interference screw, the implant can also be some other implant used in ACL/PCL reconstruction, such as a wedge, pin, anchor, nail, bolt or staple.

The invention claimed is:

1. A surgical implant made of a manufacturing material comprising a non-aromatic polymer, non-aromatic copolymer, non-aromatic polymer mixture or non-aromatic polymer composite that dissolves in an organ system, wherein the manufacturing material is dyed with a coloring agent D&C Green No. 6, wherein the amount of the coloring agent is at most approximately 0.03 percent by weight, wherein the implant is sterilized by radiation, and wherein the implant is a fixation means.

2. The surgical implant of claim 1, wherein the manufacturing material comprises a material selected from the group consisting of lactide, glycolic acid and trimethylene carbonate.

3. The surgical implant of claim 1, wherein the amount of the coloring agent is 0.002 to 0.02 percent by weight.

4. The surgical implant of claim 1, wherein the implant is sterilized by electron radiation.

5. The surgical implant of claim 1, wherein the implant is sterilized by gamma or electron radiation at a radiation dose of at most 15 kGy.

6. The surgical implant of claim 1, wherein the implant is sterilized by gamma or electron radiation at a radiation dose of at most 25 kGy.

7. The surgical implant of claim 1, wherein the implant is made at least partly in a clean room environment of classification 10,000 or better by using a melt machining method, and the implant is sterilized by gamma or electron radiation at a minimum radiation dose of 10 kGy.

8. The surgical implant of claim 1, wherein the implant is a fixation means used in ACL/PCL surgery.

9. The surgical implant of claim 1, wherein the fixation means is selected from the group consisting of an interference screw, a wedge, a pin, an anchor, a nail, a bolt and a staple.

10. The surgical implant of claim 7, wherein the melt machining method is injection molding or extrusion.

11. A surgical implant used in endoscopic surgery made of a manufacturing material comprising a non-aromatic polymer, non-aromatic copolymer, non-aromatic polymer mixture or non-aromatic polymer composite that dissolves in an organ system, wherein the manufacturing material is dyed with a coloring agent D&C Green No. 6, wherein the amount of the coloring agent is at most approximately 0.03 percent by weight, wherein the implant is sterilized by radiation, and wherein the implant is a fixation means.

12. The surgical implant of claim 11, wherein the fixation means is selected from the group consisting of an interference screw, a wedge, a pin, an anchor, a nail, a bolt and a staple.

* * * * *